United States Patent
Guo et al.

(10) Patent No.: US 12,258,392 B2
(45) Date of Patent: Mar. 25, 2025

(54) ANTI-IL-25 ANTIBODIES AND USE THEREOF

(71) Applicants: Suzhou Kanova Biopharmaceutical Co., Ltd., Jiangsu (CN); Beijing Kanova Biopharmaceutical Co., Ltd., Beijing (CN)

(72) Inventors: Li Guo, Beijing (CN); Tiantian Sun, Beijing (CN); Xiaoxu Qi, Beijing (CN); Chen Dong, Beijing (CN)

(73) Assignees: Suzhou Kanova Biopharmaceutical Co., Ltd., Jiangsu (CN); Beijing Kanova Biopharmaceutical Co., Ltd., Beijing (CN)

( * ) Notice: Subject to any disclaimer, the term of this patent is extended or adjusted under 35 U.S.C. 154(b) by 968 days.

(21) Appl. No.: 17/287,367

(22) PCT Filed: Nov. 19, 2018

(86) PCT No.: PCT/CN2018/116170
§ 371 (c)(1),
(2) Date: Apr. 21, 2021

(87) PCT Pub. No.: WO2020/102935
PCT Pub. Date: May 28, 2020

(65) Prior Publication Data
US 2021/0332123 A1 Oct. 28, 2021

(51) Int. Cl.
| | |
|---|---|
| *A61K 39/395* | (2006.01) |
| *A61P 11/06* | (2006.01) |
| *C07K 16/24* | (2006.01) |
| *A61K 39/00* | (2006.01) |

(52) U.S. Cl.
CPC ........ *C07K 16/244* (2013.01); *A61K 39/3955* (2013.01); *A61P 11/06* (2018.01); *A61K 2039/505* (2013.01); *C07K 2317/24* (2013.01); *C07K 2317/33* (2013.01); *C07K 2317/565* (2013.01); *C07K 2317/92* (2013.01)

(58) Field of Classification Search
CPC .. A61K 39/395; A61K 39/3955; C07K 16/24; C07K 16/244
See application file for complete search history.

(56) References Cited

U.S. PATENT DOCUMENTS

2016/0083466 A1* 3/2016 Orengo ................ C07K 16/244
424/142.1

FOREIGN PATENT DOCUMENTS

| CN | 102245638 A | 11/2011 |
|---|---|---|
| CN | 103097416 A | 5/2013 |
| CN | 107207589 A | 9/2017 |
| JP | 2012503979 A | 2/2012 |
| JP | 2013523132 A | 6/2013 |
| JP | 2017533888 A | 11/2017 |
| WO | WO-2008/129263 A1 | 10/2008 |
| WO | WO-2011/123507 A1 | 10/2011 |
| WO | WO-2016/049000 A2 | 3/2016 |
| WO | WO-2017/160587 A1 | 9/2017 |

OTHER PUBLICATIONS

Lloyd et al., Protein Engineering, Design & Selection, 2009, vol. 22(3):159-168.*
Goel et al., J. Immunol., 2004, vol. 173(12):7358-7367.*
Knappik et al., J. Mol. Biol., 2000, vol. 296(1):57-86.*
Rabia et al., Biochem. Eng. J., 2018, vol. 137:365-374.*
Office Action issued in Chinese Patent Application No. 201880096840.9 on Jul. 20, 2022.
Search Report issued in European Application No. 18 940 675.4 on Sep. 12, 2022.
Yao et al "Characteristics of IL-25 and Allergen-Induced Airway Fibrosis in a Murine Model of Asthma" Respirology vol. 20, pp. 730-738, 2015.
Eric Rouvier, et al. "CTLA-8, Cloned from an Activated T Cell, Bearing AU-Rich Messenger RNA Instability Sequences, and Homologous to a Herpesvirus Saimiri Gene." The Journal of Immunology. Jun. 15, 1993. vol. 150, No. 12. pp. 5445-5456.
Eric AF Simoes, et al. "Respiratory syncytial virus infection." The Lancet. Sep. 4, 1999. vol. 354. pp. 847-852.
Guohua Pan, et al. "Forced Expression of Murine-IL-17E Induces Growth Retardation, Jaundice, a Th2-Biased Response, and Multiorgan Inflammation in Mice." The Journal of Immunology. 2001. pp. 6559-6567.
Madeline M. Fort, et al. "IL-25 Induces IL-4, IL-5, and IL-13 and Th2-Associated Pathologies in Vivo." Immunity. Dec. 2001. vol. 15. pp. 985-995.
Mee Rhan Kim, et al. "Transgenic overexpression of human-IL-17E results in eosinophilia, B-lymphocyte hyperplasia, and altered antibody production." Blood. Oct. 1, 2002. vol. 100, No. 7. p. 2330.
Yui-His Wang, et al. "IL-25 augments type 2 immune responses by enhancing the expansion and functions of TSLP-DC-activated Th2 memory cells." The Journal of Experimental Medicine. Jul. 16, 2007. vol. 204, No. 8. pp. 1837-1847.
David G. Denardo, et al. "CD4+ Cells Regulate Pulmonary Metastasis of Mammary Carcinomas by Enhancing Protumor Properties of Macrophages." Cancer Cell. Aug. 4, 2009. vol. 16. pp. 91-102.
Xin-Jun Cai, et al. "Progress on anti-asthma agents targeted for cytokine." Chinese Journal of Clinical Pharmacology Therapeutics. 2010. vol. 15, Section 3. pp. 350-355.
Gerard E. Kaiko, et al. "NK Cell Deficiency Predisposes to Viral-Induced Th2-Type Allergic Inflammation via Epithelial-Derived IL-25." The Journal of Immunology. Sep. 20, 2010. pp. 4681-4690.
Seon Hee Chang, et al. "Signaling of interleukin-17 family cytokines in immunity and inflammation." Cellular Signaling. 2011. vol. 23. pp. 1069-1975.

(Continued)

*Primary Examiner* — Xiaozhen Xie
(74) *Attorney, Agent, or Firm* — Morse, Barnes-Brown & Pendleton, P.C.; Martin Z. Zhang, Esq.

(57) ABSTRACT

The present invention provides anti-IL-25 antibodies that are directed against (human) IL-25, nucleic acids that encode such antibodies, compositions, and in particular pharmaceutical compositions that comprise such antibodies; and uses of such antibodies and compositions.

13 Claims, 4 Drawing Sheets

Specification includes a Sequence Listing.

(56) References Cited

OTHER PUBLICATIONS

Yoichiro Iwakura, et al. "Functional Specialization of Interleukin-17 Family Members." Immunity Review. Feb. 25, 2011. vol. 34. pp. 149-162.
Chris J. Corrigan, et al. "Allergen-induced expression of IL-25 and IL-25 receptor in atopic asthmatic airways and late-phase cutaneous responses." J Allergy Clin Immunol. Jul. 2011. vol. 128, No. 1. pp. 116-124.
First Office Action issued in Japanese Patent Application No. 2021-528846. Mar. 28, 2022. Japan Patent Office.
First Office Action issued in Chinese Patent Application No. 201880096840.9. May 19, 2022. China National Intellectual Property Administration.

* cited by examiner (A)

(B)

ANTI-IL-25 ANTIBODIES AND USE THEREOF

CROSS REFERENCE TO RELATED APPLICATIONS

This application is the National Stage of International Application No. PCT/CN2018/116170, filed on Nov. 19, 2018. The content of this application is hereby incorporated by reference in its entirety.

FIELD OF THE INVENTION

The present invention relates to anti-IL-25 antibodies that are directed against (human) IL-25; to nucleic acids that encode such antibodies; to compositions, and in particular pharmaceutical compositions, that comprise such antibodies; and to uses of such antibodies and compositions.

BACKGROUND ART

IL-25 is a 20 KDa protein mostly known as IL-17E, encoded by chromosome 14, and contains 117 amino acids. Cytokine IL-17 family consists of 6 members; IL-17A to IL-17F, among which IL-25 (i.e., IL-17E) has a unique structure and function (Iwakura Y, et al., *Immunity* 2011; 34: 149-162; Chang S H, Dong C. *Cell Signal* 2011; 23: 1069-1075.). The receptor of IL-25 (IL-17BR) is highly expressed in main Th2 cells (Rouvier E, et al., *J. Immunol.*, 1993; 150:5445-5456). IL-25 regulates internal safety of adaptive immune responses, which leads to begin allergic diseases and plays a role in stimulation of pulmonary mucosal cells and fibroblasts. IL-25 can also have some effects on production of other cytokines. For instance, production of IL-25 in human and mice or injection of IL-25 to animals has resulted in production of high concentrations of Th2 cytokines, including IL-4, IL-5, and IL-13. Pilot studies have shown that mRNA of IL-25 has a high expression in Th2 cells. Groups of researchers have stated that IL-25 is a strong inflammatory cytokine protein which is involved in allergic inflammations (Fort M M, et al., *Immunity* 2001; 15:985-995, Pan G, et al., *J. Immunol.*, 2001; 167:6559-6567; Kim M, et al., *Blood*, 2002; 100: 2330-2340).

Most allergic diseases result from irregularities in type 2 immune system. Several studies have confirmed that the Th2 cells and mucosal cells, macrophages, eosinophils, basophils, and pulmonary epithelial cells are the hidden producers of IL-25 (Rouvier E, et al. *J. Immunol*, 1993; 150: 5445-5456). After activation of mammary cells associated with IgE in a mouse model of asthma, a transverse relationship was observed between IL-25 and IgE. According to such findings the highest production was seen 24 h after lung infection in asthma patients. It has been suggested that production of IL-25 by airway macrophages might play a role in regulation of inflammatory responses in lungs. (Wangy Y H, et al., *J. Exp Med.* 2007; 204:1837-47).

Respiratory Syncytial Virus (RSV) increases the risk of progress in asthma among children. Up to now, several studies have been performed on the effects of deficit and decrease in NK cells in the children suffering from RSV. Yet, the important issue is how decrease in the number of NK cells in RSV infection leads to inhibition of INF-α production, progress of Th2, and increase of IL-25, eventually resulting in allergic diseases (Simoes E A, et al., *Lancet.* 1999; 354:847-52). A research conducted by Gerard Aie et al., in 2010 indicated that increase of Th2 reactions and effect of IL-25 derived from respiratory tract epithelial cells enhanced the expression of notch ligand jagged on DC cells, inflammation, and asthma (Gerard E Kaiko, et al., *J Immunol.* 2010; 185:4681-4689).

Furthermore, in some human studies, sequential single and double immunostaining was used to evaluate the numbers and phenotypes of IL-25 and IL-25R immunoreactive cells in bronchial biopsies from mild atopic subjects with asthma (n 5 10) before and 24 hours after allergen inhalation challenge and skin biopsies from atopic subjects (n=5-10) up to 72 hours after allergen subepidermal injection. The results showed that IL-25 immunoreactivity was expressed by a majority of epidermal cells in both organs at baseline and was not further augmented by challenge. IL-25R immunoreactive cells were rare in the epidermis before or after challenge. Allergen challenge was associated with significantly ($P<0.01$) increased expression of IL-25 and IL-25R immunoreactivity in the submucosa of both organs. IL-25 immunoreactivity colocalized with eosinophils, mast cells, and endothelial cells, whereas IL-25R immunoreactivity colocalized with eosinophils, mast cells, endothelial cells, and T lymphocytes. In both organs, correlations were observed between increases in IL-25 expression and the magnitudes of the late-phase allergeninduced clinical responses. (Corrigan C J, et al., J. Allergy Clin Immunol, 2011; 128: 117-124).

During breast cancer development, increased presence of leukocytes in neoplastic stroma parallels disease progression; however, the functional significance of leukocytes in regulating protumor versus antitumor immunity in the breast remains poorly understood. Utilizing the MMTV-PyMT model of mammary carcinogenesis, it has demonstrated that IL-4-expressing CD4+ T lymphocytes indirectly promote invasion and subsequent metastasis of mammary adenocarcinomas by directly regulating the phenotype and effector function of tumor-associated CD11b+Gr1-F4/80+ macrophages that in turn enhance metastasis through activation of epidermal growth factor receptor signaling in malignant mammary epithelial cells. Together, these data indicate that antitumor acquired immune programs can be usurped in protumor microenvironments and instead promote malignancy by engaging cellular components of the innate immune system functionally involved in regulating epithelial cell behavior. (DeNardo D G, et al., *Cancer cell,* 2009, 16: 91-102). Taken together, this cytokine also plays a role in the creation of allergic inflammation in asthma and autoimmune diseases as well as in treatment of cancer.

SUMMARY OF THE INVENTION

In one aspect, the present invention provides antibodies that are capable of specifically binding to human IL-25, including a murine anti-IL-25 monoclonal antibody 18H3. More particular, the invention relates to antibodies that (i) competes with murine antibody 18H3 for binding to (human) IL-25; and/or (ii) binds to the same epitope on (human) IL-25 as 18H3; and/or (iii) cross-blocks the binding of 18H3 to (human) IL-25.

In another aspect, the present invention provides an isolated nucleic acid encoding the antibody according to the invention.

In a further aspect, the present invention provides host cell comprising the nucleic acid as recited above.

In a still further aspect, the present invention provides a method of producing the antibody according to the invention comprising culturing the host cell as recited above so that the antibody is produced.

In another aspect, the present invention also provides a pharmaceutical composition comprising the antibody according to the invention and a pharmaceutically acceptable carrier.

In another aspect, the present invention further provides a method of treating diseases associated with IL-25 in a subject comprising administering to the subject an effective amount of the antibody according to the invention.

The present invention also provides use of the antibody according to the invention for the preparation of a medicament for treating diseases associated with IL-25 in a subject.

Specifically, the present invention relates to:

[1] An anti-IL-25 antibody that (i) competes with murine antibody 18H3 for binding to (human) IL-25; and/or (ii) binds to the same epitope on (human) IL-25 as 18H3; and/or (iii) cross-blocks the binding of 18H3 to (human) IL-25.

[2] The anti-IL-25 antibody according to above [1], wherein the antibody comprises a heavy chain variable region and a light chain variable region, in which the heavy chain variable region comprises:
  a) a CDR1 which comprises or essentially consists of either (i) the amino acid sequence GFSLSTSGMGLG (SEQ ID NO: 1) or (ii) an amino acid sequence that has only 3, 2 or 1 amino acid difference(s) with the amino acid sequence GFSLSTSGMGLG (SEQ ID NO: 1);
  b) a CDR2 which comprises or essentially consists of either (i) the amino acid sequence HIWWDDVKHYKPALKS (SEQ ID NO: 2) or (ii) an amino acid sequence that has only 3, 2 or 1 amino acid difference(s) with the amino acid sequence HIWWDDVKHYKPALKS (SEQ ID NO: 2); and
  c) a CDR3 which comprises or essentially consists of either (i) the amino acid sequence MGQLHYYGYDYAMDY (SEQ ID NO: 3) or (ii) an amino acid sequence that has only 3, 2 or 1 amino acid difference(s) with the amino acid sequence MGQLHYYGYDYAMDY (SEQ ID NO: 3);
and
in which the light chain variable region comprises:
  a) a CDR1 which comprises or essentially consists of either (i) the amino acid sequence SASSSVSYMY (SEQ ID NO: 4) or (ii) an amino acid sequence that has only 3, 2 or 1 amino acid difference(s) with the amino acid sequence SASSSVSYMY (SEQ ID NO: 4);
  b) a CDR2 which comprises or essentially consists of either (i) the amino acid sequence RTSNLAS (SEQ ID NO: 5) or (ii) an amino acid sequence that has only 3, 2 or 1 amino acid difference(s) with the amino acid sequence RTSNLAS (SEQ ID NO: 5); and
  c) a CDR3 which comprises or essentially consists of either (i) the amino acid sequence QLYHSYPPTWT (SEQ ID NO: 6) or (ii) an amino acid sequence that has only 3, 2 or 1 amino acid difference(s) with the amino acid sequence QLYHSYPPTWT (SEQ ID NO: 6).

[3] The anti-IL-25 antibody according to above [2], wherein the heavy chain variable region comprises a CDR1 having the amino acid sequence GFSLSTSGMGLG (SEQ ID NO: 1), a CDR2 having the amino acid sequence HIWWDDVKHYKPALKS (SEQ ID NO: 2) and a CDR3 having the amino acid sequence MGQLHYYGYDYAMDY (SEQ ID NO: 3), and the light chain variable region comprises a CDR1 having the amino acid sequence SASSSVSYMY (SEQ ID NO: 4), a CDR2 having the amino acid sequence RTSNLAS (SEQ ID NO: 5) and a CDR3 having the amino acid sequence QLYHSYPPTWT (SEQ ID NO: 6).

[4] The anti-IL-25 antibody according to any one of above [1] to [3], wherein the heavy chain variable region has at least 70%, such at least 80%, for example at least 85%, such as at least 90% or more than 95% sequence identity with the amino acid sequence of SEQ ID NO: 12, and/or the light chain variable region has at least 70%, such at least 80%, for example at least 85%, such as at least 90% or more than 95% sequence identity with the amino acid sequence of SEQ ID NO: 13.

[5] The anti-IL-25 antibody according to any one of above [1] to [4], wherein the heavy chain variable region comprises the amino acid sequence of SEQ ID NO: 7, SEQ ID NO: 8, SEQ ID NO: 9 or SEQ ID NO: 12, and/or the light chain variable region comprises the amino acid sequence of SEQ ID NO: 10, SEQ ID NO: 11 or SEQ ID NO: 13.

[6] The anti-IL-25 antibody according to above [5], wherein:
  i) the heavy chain variable region comprises the amino acid sequence of SEQ ID NO: 7, and the light chain variable region comprises the amino acid sequence of SEQ ID NO: 10;
  ii) the heavy chain variable region comprises the amino acid sequence of SEQ ID NO: 7, and the light chain variable region comprises the amino acid sequence of SEQ ID NO: 11;
  iii) the heavy chain variable region comprises the amino acid sequence of SEQ ID NO: 8, and the light chain variable region comprises the amino acid sequence of SEQ ID NO: 10;
  iv) the heavy chain variable region comprises the amino acid sequence of SEQ ID NO: 8, and the light chain variable region comprises the amino acid sequence of SEQ ID NO: 11;
  v) the heavy chain variable region comprises the amino acid sequence of SEQ ID NO: 9, and the light chain variable region comprises the amino acid sequence of SEQ ID NO: 10;
  vi) the heavy chain variable region comprises the amino acid sequence of SEQ ID NO: 9, and the light chain variable region comprises the amino acid sequence of SEQ ID NO: 11; or
  vii) the heavy chain variable region comprises the amino acid sequence of SEQ ID NO: 12, and the light chain variable region comprises the amino acid sequence of SEQ ID NO: 13.

[7] The anti-IL-25 antibody according to above [1], which is a monoclonal antibody, and/or a murine, humanized or chimeric antibody, preferably of IgG class.

[8] The anti-IL-25 antibody according to above [1], which is an antibody fragment that binds (human) IL-25, preferably selected from the group consisting of Fv, Fab, Fab-SH, Fab'-SH, Fab', Fab-C, Fab'-C, Fab'-C—SH, Fab-C—SH, scFv, diabody, or F(ab')$_2$; diabodies; linear antibodies; single-chain antibody molecules (e.g. scFv); and multispecific antibodies formed from antibody fragments.

[9] An isolated nucleic acid encoding the antibody of any one of above [1] to [8].

[10] A host cell comprising the nucleic acid of above [9].

[11] A method of producing the antibody of any one of above [1] to [8] comprising culturing the host cell of above [10] so that the antibody is produced.

[12] A pharmaceutical composition comprising the antibody of any one of above [1] to [8] and a pharmaceutically acceptable carrier.

[13] A method of treating diseases associated with IL-25 in a subject comprising administering to the subject an effective amount of the antibody of any one of above [1] to

[8], the nucleic acid of above [9], the host cell of above [10] or the pharmaceutical composition of above [12].

[14] The method according to above [13], wherein the subject is a mammal, preferably rat, mouse, monkey, or human.

[15] The method according to above [13] or [14], wherein the diseases associated with IL-25 are selected from autoimmune disorders, inflammatory diseases or cancers wherein IgE, IL-4, IL-5 and/or IL-13 are overexpressed/overproduced, preferably allergic (inflammatory) diseases, and more preferably selected from asthma (e.g., allergic asthma), atopic dermatitis, atopic allergic diseases, allergic rhinitis, hay fever, allergic conjunctivitis, eczema, food allergies, psoriasis, psoriatic arthritis, ankylosing spondylitis, rheumatoid arthritis (RA), multiple sclerosis (MS), systemic lupus, osteoarthritis or inflammatory bowel disorder (IBD).

[16] Use of the antibody of any one of above [1] to [8], the nucleic acid of above [9], the host cell of above [10] or the pharmaceutical composition of above [12] for the preparation of a medicament for treating diseases associated with IL-25 in a subject.

[17] The antibody of any one of above [1] to [8], the nucleic acid of above [9], the host cell of above [10] or the pharmaceutical composition of above [12] for use in a method of treating diseases associated with IL-25 in a subject.

DESCRIPTION OF EMBODIMENTS

Figure 1:
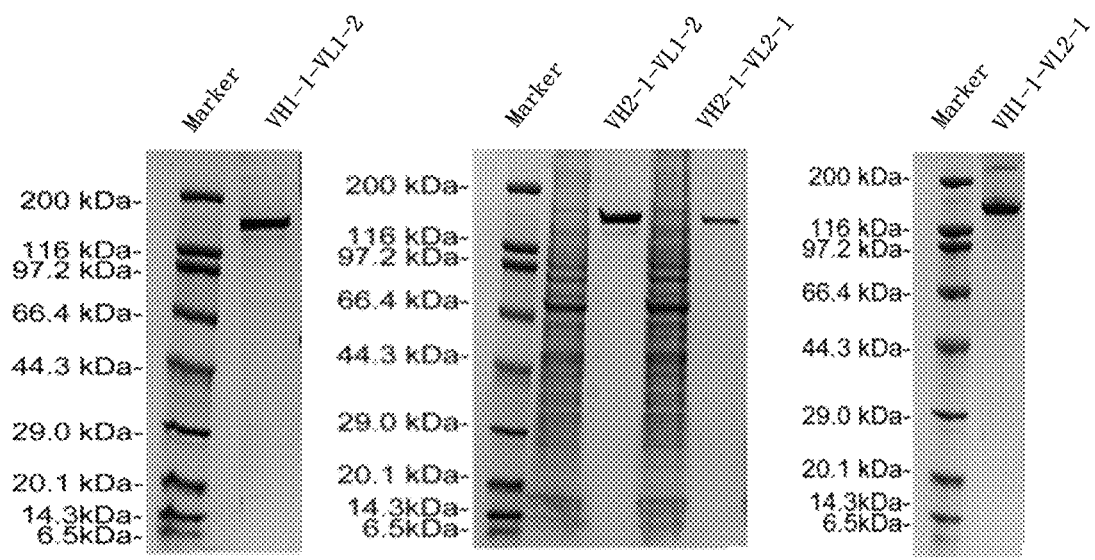
FIG. 1 illustrates expression and purification of anti-IL-25 antibodies, as described in Example 2, wherein VH1-1-VL1-2 represents the antibody formed by the variable heavy chain domain (VH1-1) and the variable light chain domain (VL1-2), and such a nomenclature applies to other antibodies. For example, VH2-1-VL1-2 represents the antibody formed by VH2-1 and VL1-2, VH2-1-VL2-1 represents the antibody formed by VH2-1 and VL2-1, VH1-1-VL2-2 represents the antibody formed by VH1-1 and VL2-2, and VH1-2-VL2-1 represents the antibody formed by VH1-2 and VL2-1.

While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

I. Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms "anti-IL-25 antibody" and "an antibody that binds to IL-25" refer to an antibody that is capable of binding IL-25 with sufficient affinity such that the antibody is useful as a diagnostic and/or therapeutic agent in targeting IL-25. In some embodiments, the extent of binding of an anti-IL-25 antibody to an unrelated, non-IL-25 protein is less than about 10% of the binding of the antibody to IL-25 as measured, e.g., by SPR. In certain embodiments, an antibody that binds to IL-25 has a dissociation constant ($K_D$) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-IL-25 antibody binds to an epitope of IL-25 that is conserved among IL-25 from different species (e.g., mice, human, and cynomolgus monkey).

An "antibody fragment" refers to a molecule other than an intact antibody that comprises a portion of an intact antibody and that binds the antigen to which the intact antibody binds. Examples of antibody fragments include but are not limited to Fv, Fab, Fab-SH, Fab'-SH, Fab', Fab-C, Fab'-C, Fab'-C—SH, Fab-C—SH, scFv, diabody, or F(ab')2; diabodies; linear antibodies; single-chain antibody molecules (e.g. scFv); and multispecific antibodies formed from antibody fragments.

As used herein, a "Fab" refers to an antibody that comprises a heavy chain constant region that comprises the CH1 domain, or a sufficient portion of the CH1 domain to form a disulfide bond with the light chain constant region, but does not contain a CH2 domain or a CH3 domain. As used herein, a Fab may comprise one or more amino acids of the hinge region. Thus, as used herein, the term "Fab" encompasses Fab' antibodies. A Fab may comprise additional non-native amino acids, such as a C-terminal cysteine, in which case it may be referred to as a Fab-C. As discussed below, the term Fab-C also encompasses Fabs comprising native amino acids of the hinge region, including a native cysteine at the C-terminus. In some embodiments, a Fab comprises an engineered cysteine (i.e., a Fab may be a THIOMAB).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. Preferably, the antibody of the invention is of IgG class.

The term "epitope" refers to the particular site on an antigen molecule to which an antibody binds.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., WH. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

As used herein, when comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides as described herein, the term "amino acid difference" refers to an insertion, deletion or substitution of a single amino acid residue on a position of the specified CDR sequence, compared to the CDR sequence under consideration. In this respect, the amino acid sequence under consideration may be an amino acid sequence that is derived from the specified amino acid sequence according by means of affinity maturation using one or more techniques of affinity maturation known per se. Preferably, the "amino acid difference" is a "conservative" amino acid substitution, as defined below.

"Percent (%) (amino acid) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As used herein, the term "cross-block" means the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. One particularly suitable quantitative cross-blocking assay uses a BIAcore instrument which can measure the extent of interactions using surface plasmon resonance technology. Another suitable quantitative cross-blocking assay uses an ELISA-based approach to measure competition between immunoglobulins, antibodies, immunoglobulin single variable domains, polypeptides or other binding agents in terms of their binding to the target.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Composition and Methods

A. Exemplary Anti-IL-25 Antibodies

Provided herein are isolated antibodies that bind to (e.g., human) IL-25. In particular, provided herein are antibodies that bind IL-25 with a very high affinity, such as with a $K_D$ of less than 100 pM, or less than 75 pM, or less than 50 pM, or less than 10 pM (as determined by the method(s) described in Examples). Further, provided herein are antibodies, such as Fabs, that are highly soluble. In any of the embodiments described herein, the antibodies may be monoclonal antibodies. In some embodiments, the antibodies may be human antibodies, humanized antibodies, or chimeric antibodies. In any of the embodiments described herein, the antibodies may be Fab fragments.

In some embodiments, the invention provides an anti-IL-25 antibody that (i) competes with murine antibody 18H3 for binding to (human) IL-25; and/or (ii) binds to the same epitope on (human) IL-25 as 18H3; and/or (iii) cross-blocks the binding of 18H3 to (human) IL-25.

In some embodiments, the antibody comprises a heavy chain variable region and a light chain variable region, in which the heavy chain variable region comprises:
  a) a CDR1 which comprises or essentially consists of either (i) the amino acid sequence GFSLSTSGMGLG (SEQ ID NO: 1) or (ii) an amino acid sequence that has only 3, 2 or 1 amino acid difference(s) with the amino acid sequence GFSLSTSGMGLG (SEQ ID NO: 1);
  b) a CDR2 which comprises or essentially consists of either (i) the amino acid sequence HIWWDDVKHYKPALKS (SEQ ID NO: 2) or (ii) an amino acid sequence that has only 3, 2 or 1 amino acid difference(s) with the amino acid sequence HIWWDDVKHYKPALKS (SEQ ID NO: 2); and
  c) a CDR3 which comprises or essentially consists of either (i) the amino acid sequence MGQLHYYGYDYAMDY (SEQ ID NO: 3) or (ii) an amino acid sequence that has only 3, 2 or 1 amino acid difference(s) with the amino acid sequence MGQLHYYGYDYAMDY (SEQ ID NO: 3);
and
in which the light chain variable region comprises:
  a) a CDR1 which comprises or essentially consists of either (i) the amino acid sequence SASSSVSYMY (SEQ ID NO: 4) or (ii) an amino acid sequence that has only 3, 2 or 1 amino acid difference(s) with the amino acid sequence SASSSVSYMY (SEQ ID NO: 4);
  b) a CDR2 which comprises or essentially consists of either (i) the amino acid sequence RTSNLAS (SEQ ID NO: 5) or (ii) an amino acid sequence that has only 3, 2 or 1 amino acid difference(s) with the amino acid sequence RTSNLAS (SEQ ID NO: 5); and
  c) a CDR3 which comprises or essentially consists of either (i) the amino acid sequence QLYHSYPPTWT (SEQ ID NO: 6) or (ii) an amino acid sequence that has only 3, 2 or 1 amino acid difference(s) with the amino acid sequence QLYHSYPPTWT (SEQ ID NO: 6).

In some embodiments, the heavy chain variable region comprises a CDR1 having the amino acid sequence GFSLSTSGMGLG (SEQ ID NO: 1), a CDR2 having the amino acid sequence HIWWDDVKHYKPALKS (SEQ ID NO: 2) and a CDR3 having the amino acid sequence MGQLHYYGYDYAMDY (SEQ ID NO: 3), and the light chain variable region comprises a CDR1 having the amino acid sequence SASSSVSYMY (SEQ ID NO: 4), a CDR2 having the amino acid sequence RTSNLAS (SEQ ID NO: 5) and a CDR3 having the amino acid sequence QLYHSYPPTWT (SEQ ID NO: 6). Preferably, the heavy chain variable region has at least 70%, such at least 80%, for example at least 85%, such as at least 90% or more than 95% (e.g., at least 90%, 91%, 92%, 93%, 94%, 95%, 96%, 97%, 98%, 99%, or 100%) amino acid sequence identity with the amino acid sequence of SEQ ID NO: 12, and/or the light chain variable region has at least 70%, such at least 80%, for example at least 85%, such as at least 90% or more than 95% (e.g., at least 90%, 91%, 92%, 93%, 94%, 95%, 96%, 97%, 98%, 99%, or 100%) amino acid sequence identity with the amino acid sequence of SEQ ID NO: 13. In some embodiments, the heavy/light chain variable region contains substitutions (e.g., conservative substitutions), insertions, or deletions relative to the reference sequence, but an anti-IL-25 antibody comprising that sequence retains the ability to bind to IL-25. In certain embodiments, a total of 1 to 10 (such as 1, 2, 3, 4, 5, 6, 7, 8, 9 and 10) amino acids have been substituted, inserted and/or deleted in any one or more of SEQ ID NOs: 1 to 6, 12 and 13. In certain embodiments, substitutions, insertions, or deletions occur in regions outside the CDRs (i.e., in the FRs).

In any of the embodiments herein, an anti-IL-25 antibody may be humanized. In some embodiments, an anti-IL-25 antibody comprises CDRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the mutations described herein.

More preferably, the heavy chain variable region comprises the amino acid sequence of SEQ ID NO: 7, SEQ ID NO: 8, SEQ ID NO: 9 or SEQ ID NO: 12, and/or the light chain variable region comprises the amino acid sequence of SEQ ID NO: 10, SEQ ID NO: 11 or SEQ ID NO: 13. Most preferably, in the anti-IL-25 antibody according to present invention, i) the heavy chain variable region comprises the amino acid sequence of SEQ ID NO: 7, and the light chain variable region comprises the amino acid sequence of SEQ ID NO: 10; ii) the heavy chain variable region comprises the amino acid sequence of SEQ ID NO: 7, and the light chain variable region comprises the amino acid sequence of SEQ ID NO: 11; iii) the heavy chain variable region comprises the amino acid sequence of SEQ ID NO: 8, and the light chain variable region comprises the amino acid sequence of SEQ ID NO: 10; iv) the heavy chain variable region comprises the amino acid sequence of SEQ ID NO: 8, and the light chain variable region comprises the amino acid sequence of SEQ ID NO: 11; v) the heavy chain variable region comprises the amino acid sequence of SEQ ID NO: 9, and the light chain variable region comprises the amino acid sequence of SEQ ID NO: 10; vi) the heavy chain variable region comprises the amino acid sequence of SEQ ID NO: 9, and the light chain variable region comprises the amino acid sequence of SEQ ID NO: 11; or vii) the heavy chain variable region comprises the amino acid sequence of SEQ ID NO: 12, and the light chain variable region comprises the amino acid sequence of SEQ ID NO: 13.

In another aspect, an anti-IL-25 antibody is provided, wherein the antibody comprises a VH as in any of the embodiments provided above, and a VL as in any of the embodiments provided above.

In a further aspect, provided herein are antibodies that bind to the same epitope as an anti-IL-25 antibody in any of the embodiments provided above.

In a further aspect of the invention, an anti-IL-25 antibody according to any of the above embodiments is a monoclonal antibody, including a human antibody. In some embodiments, an anti-IL-25 antibody is an antibody fragment, e.g., a Fv, Fab, Fab-SH, Fab'-SH, Fab', Fab-C, Fab'-C, Fab'-C—SH, Fab-C—SH, scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, the anti-IL-25 antibody is a Fab.

B. Recombinant Methods and Compositions

Antibodies may be produced using recombinant methods and compositions. In some embodiments, isolated nucleic acid encoding an anti-IL-25 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided.

In some embodiments, the host cell is eukaryotic, e.g. HEK293 cell, a Chinese Hamster Ovary (CHO) cell or lymphoid cell (e.g., Y0, NS0, Sp20 cell). In some embodiments, a method of making an anti-IL-25 antibody is provided, wherein the method comprises culturing a host cell comprising a nucleic acid encoding the antibody, as provided above, under conditions suitable for expression of the antibody, and optionally recovering the antibody from the host cell (or host cell culture medium).

C. Assays

Anti-IL-25 antibodies provided herein may be identified, screened for, or characterized for their physical/chemical properties and/or biological activities by various assays known in the art. In some embodiments, an antibody of the invention is tested for its antigen binding activity, e.g., by known methods such as ELISA, SPR, BIACore®, FACS, or Western blot.

In another aspect, competition assays may be used to identify an antibody that competes with any of the antibodies described herein for binding to IL-25. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

D. Methods and Compositions for Diagnostics and Detection

In certain embodiments, any of the anti-IL-25 antibodies provided herein is useful for detecting the presence of IL-25 in a biological sample. The term "detecting" as used herein encompasses quantitative or qualitative detection. A "biological sample" comprises, e.g., a cell or tissue.

In some embodiments, an anti-IL-25 antibody for use in a method of diagnosis or detection is provided. In a further aspect, a method of detecting the presence of IL-25 in a biological sample is provided. In certain embodiments, the method comprises contacting the biological sample with an anti-IL-25 antibody as described herein under conditions permissive for binding of the anti-IL-25 antibody to IL-25, and detecting whether a complex is formed between the anti-IL-25 antibody and IL-25 in the biological sample. Such method may be an in vitro or in vivo method. In some embodiments, an anti-IL-25 antibody is used to select subjects eligible for therapy with an anti-IL-25 antibody, e.g. where IL-25 is a biomarker for selection of patients.

E. Pharmaceutical Formulations

The invention also relates to a pharmaceutical composition comprising the antibody of the invention and a pharmaceutically acceptable carrier.

Pharmaceutical formulations of an anti-IL-25 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives; metal complexes (e.g. Zn-protein complexes); and/or non-ionic surfactants such as polyethylene glycol (PEG), and the like.

The formulation herein may also contain more than one active ingredient as necessary for the particular indication being treated. In some embodiments, the active ingredients have complementary activities that do not adversely affect each other.

F. Therapeutic Methods and Compositions

Any of the anti-IL-25 antibodies provided herein may be used in methods, e.g., therapeutic methods.

The invention also relates to a method of treating diseases associated with IL-25 in a subject comprising administering to the subject an effective amount of an antibody, nucleic acid, host cells or a pharmaceutical composition according to present invention. In particular, said effective amount may be an amount that is sufficient to modulate IL-25, its biological or pharmacological activity, and/or the biological pathways or signaling in which IL-25 is involved.

A "subject" according to any of the embodiments herein may be a mammal, preferably rat, mouse, monkey, or human.

The anti-IL-25 antibody may be administered by any suitable means, including parenteral, subcutaneous, intraperitoneal, intravitreal, intrapulmonary, and intranasal, and, if desired for local immunosuppressive treatment, intralesional administration. Parenteral infusions include intramuscular, intravenous, intraarterial, intraperitoneal, intravitreal, and subcutaneous administration. In addition, the antibody is suitably administered by pulse infusion, particularly with declining doses of the antibody, or antibody variant thereof or fragment thereof (e.g. antigen-binding fragment). In some embodiments, the dosing is given by injections, such as intravenous or subcutaneous injections, depending in part on whether the administration is brief or chronic.

The anti-IL-25 antibody according to present invention may be used to prevent and/or treat a disease associated with IL-25. Such a disease may be associated with excessive or uncontrolled IL-25 production/expression/activity. For example, the diseases associated with IL-25 may be selected from autoimmune disorders or inflammatory diseases wherein IgE, IL-4, IL-5 and/or IL-13 are overexpressed, preferably allergic (inflammatory) diseases, and more preferably selected from asthma (e.g., allergic asthma), atopic dermatitis, atopic allergic diseases, allergic rhinitis, hay fever, allergic conjunctivitis, eczema, food allergies, psoriasis, psoriatic arthritis, ankylosing spondylitis, rheumatoid arthritis (RA), multiple sclerosis (MS), systemic lupus, osteoarthritis or inflammatory bowel disorder (IBD).

The invention also relates to use of the anti-IL-25 antibody, nucleic acid, host cells or pharmaceutical composition according to present invention for the preparation of a medicament for treating diseases associated with IL-25 in a subject.

EXAMPLES

The following are examples of methods and compositions of the invention. It is understood that various other embodiments may be practiced, given the general description provided above.

Example 1 Generation of Anti-IL-25 Antibodies

IL-25 KO mice (16-18 g, 6 weeks old, n=3, Provided by Prof Chen Dong laboratory at Tsinghua University) were immunized by subcutaneous injection with 10 μg human IL-25 protein (NCBI Gene ID: 64806) produced in-house in accordance with the general standard method for protein expression with complete Freund adjuvant (Sigma-Aldrich, Cat #F6881). Immunization was repeated 5 times at an interval of 3 days. 3 days after the final boost, the lymph nodes close to the injection site were carefully dissected out. The lymphocytes were fused with Ag8.653 myeloma cells (Sigma-Aldrich, Cat #85011420) in the presence of PEG1500 (Polyethylene Glycol 1500, Roche T M. Cat #:783641, 10×4 ml in 75 mM Hepes, PEG 50% W/V), and cloned with HAT selection (Sigma cat #: H0262) and HFCS (Hybridoma Fusion and cloning Cloning Supplement, 50×, Roche cat #: 11-363-735-001). The hybridoma supernatants were screened for the production of antibodies that can bind to human IL-25 by ELISA. Furthermore, the antagonistic anti-IL-25 mAb was selected according to the cell-based function assay (see Raig R, et al, Gut 2000; 46:350-358). The selected murine IL-25 antagonistic mAb candidate (18H3, mIgG1) was sequenced (SEQ ID No. 12 & 13) and then humanized using CDR grafting and back mutation.

Antibody humanization by CDR grafting: A selection of acceptor frameworks was made. The variable domain sequences of parental antibody were searched in the database of human germline using NCBI Ig-Blast (www.ncbi.nlm.nih.gov/projects/igblast/). The six CDR sequences of heavy chain and light chain (SEQ ID NOs: 1-6) of murine IL-25 antagonistic mAb candidate (18H3) are shown below respectively. Five diverse human acceptors (i.e. human variable domains with high homology to the parental antibody) for each heavy chain and light chain were chosen. The CDRs of human acceptors were replaced with their mouse counterparts, resulting in humanized variable domain sequences. Five humanized heavy chains and five humanized light chains were designed, synthesized and inserted into an expression vector, respectively. The humanized antibodies were expressed, and then used for affinity ranking test. The antibodies with the strongest binding affinity (VH1-VL2, VH1-VL1, VH2-VL2 and VH2-VL1) were selected for back mutation. Among the variants, the VH1-1-VL2-1, VH1-1-VL1-2, VH2-1-VL1-2 and VH2-1-

VL2-1 were selected based on binding and functional assays (SEQ ID NOs: 7-10).

CDR1H amino acid sequence
(SEQ ID NO: 1)
GFSLSTSGMGLG

CDR2H amino acid sequence
(SEQ ID NO: 2)
HIWWDDVKHYKPALKS

CDR3H amino acid sequence
(SEQ ID NO: 3)
MGQLHYYGYDYAMDY

CDR1L amino acid sequence
(SEQ ID NO: 4)
SASSSVSYMY

CDR2L amino acid sequence
(SEQ ID NO: 5)
RTSNLAS

CDR3L amino acid sequence
(SEQ ID NO: 6)
QLYHSYPPTWT

Variable heavy chain domain (VH1-1) amino acid sequence
(SEQ ID NO: 7)
QVTLKESGPTLVKPTQTLTLTCTFSGFSLSTSGMGLGWIRQPPGKALEWL

AHIWWDDVKHYKPALKSRLTITKDTSKNQVVLTMTNVDPVDTATYYCARM

GQLHYYGYDYAMDYWGQGTLVTVSS

Variable heavy chain domain (VH2-1) amino acid sequence
(SEQ ID NO: 8)
QVTLRESGPALLKPTQTLTLTCTFSGFSLSTSGMGLGWIRQPPGKALEWL

AHIWWDDVKHYKPALKSRLTISKDTSKNQVVLTITNVDPVDTATYYCARM

GQLHYYGYDYAMDYWGQGTLVTVSS

Variable heavy chain domain (VH1-2) amino acid sequence
(SEQ ID NO: 9)
MGWSWILLFLLSVTAGVHSQVTLKESGPTLLKPTQTLTLTCTFSGFSLST

SGMGLGWIRQPPGKALEWLAHIWWDDVKHYKPALKSRLTITKDTSKNQVV

LTITNVDPVDTATYYCARMGQLHYYGYDYAMDYWGQGTLVTVSS

Variable light chain domain (VL2-1) amino acid sequence
(SEQ ID NO: 10)
DIQLTQSPSFLSASVGDRVTITCSASSSVSYMYWYQQKPGKAPKPLIYRT

SNLASGVPSRFSGSGSGTEYTLTISSMQPEDFATYYCQLYHSYPPTWTFG

QGTKLEIK

Variable light chain domain (VL1-2) amino acid sequence
(SEQ ID NO: 11)
EIVLTQSPATLSASPGERVTISCSASSSVSYMYWYQQKPGQAPRPLIYRT

SNLASGVPARFSGSGSGTDYTLTISSMEPEDFATYYCQLYHSYPPTWTFG

QGTKLEIK

Amino acid sequence of variable heavy chain of 18H3
(SEQ ID NO: 12)
QVTLKESGPGILQPSQTLSLTCSFSGFSLSTSGMGLGWIRQPSGKGLEWL

AHIWWDDVKHYKPALKSRLTISKDISSSQVFLTIASVDTADTATYYCARM

GQLHYYGYDYAMDYWGQGTSVTVSS

Amino acid sequence of variable light chain of 18H3
(SEQ ID NO: 13)
QIVLTQSPAIMSASPGEKVTISCSASSSVSYMYWYQQKPGSSPKPWIYRT

SNLASGVPARFSGSGSGTSYSLTISSMEAEDAATYYCQLYHSYPPTWTFG

GGTKLEIK

Example 2. Expression and Purification of Anti-IL-25 Antibodies

The DNA sequences encoding humanized IgG heavy chain (variable domain amino acid sequence of SEQ ID NO: 7, 8 or 9) and light chain (variable amino acid sequence of SEQ ID NO: 10 or 11) were synthesized and inserted into pCDNA3.1 vector (commercially available from Life Technology) to construct expression plasmids of full-length IgGs. Expression of parental antibody was conducted in 100 ml HEK293 cell culture (HEK293 cell is commercially available from ThermoFisher Scientific) and the supernatants were purified with protein A affinity column (commercially available from GE Healthcare life Science). The purified antibody was buffer-exchanged into PBS using PD-10 desalting column (commercially available from Thermofisher Scientific). The concentration and purity of the purified protein were determined by OD280 and SDS-PAGE, respectively. The humanized antibodies were expressed in 30 ml HEK293 cell culture. The cells were spun down. The supernatants were filtered and conducted with SDS-PAGE analysis (FIG. 1).

Example 3. SPR Analysis the Binding Affinity of Anti-IL-25 Antibody to Human IL-25

Anti-human Fc gamma specific antibody (Jackson Immuno Research, Lot no. 124448, Code. 109-008-098) was immobilized onto the Biacore T200 sensor chip using amine coupling method. Four antibodies secreted to the culture medium plus the parental antibody were injected and captured by anti-human Fc antibody via Fc (capture phase) individually. After equilibration, IL-25 was injected for 300 seconds (association phase) followed by the injection of running buffer for 1200 s (dissociation phase). Responses of reference flow cell (flow cell 1) were subtracted from those of humanized antibodies flow cells during each cycle. The surface was regenerated before the injection of another humanized antibody. The process was repeated until all antibodies are analyzed. The off-rates of humanized antibodies were obtained from fitting the experimental data locally to 1:1 interaction model using the Biacore T200 evaluation software. The antibodies were ranked by their dissociation rate constants (off-rates, $K_d$). The binders that interact with IL-25 with similar affinity to parental antibody were selected (Table 1).

TABLE 1

Affinity measurement data

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| VH1-1 + VL1-2$^a$ | | 1.06E+06 | 2.84E−04 | 2.67E−10 | 75.2 | 3.02E−01 |
| VH1-1 + VL2-1 | | 9.57E+05 | 2.59E−04 | 2.71E−10 | 77.7 | 2.35E−01 |
| VH2-1 + VL1-2 | IL-25 | 1.19E+06 | 3.27E−04 | 2.75E−10 | 71.2 | 4.00E−01 |
| VH2-1 + VL2-1 | | 1.17E+06 | 3.53E−04 | 3.02E−10 | 54.7 | 2.04E−01 |
| 18H3 | | 7.85E+05 | 2.67E−04 | 3.40E−10 | 18.3 | 3.85E−02 |

$^a$VH1-1 + VL1-2 represents the antibody formed by VH1-1 and VL1-2. Such a nomenclature applies to other antibodies.

Example 4. Binding to Human IL-25 as Measured by ELISA

Figure 2:
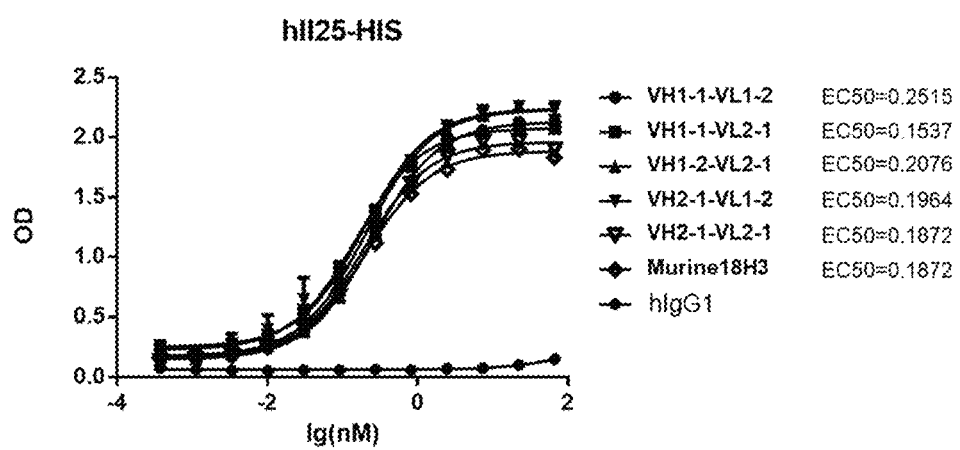
FIG. 2 illustrates binding of anti-IL-25 antibodies to human IL-25 (hIl25-HIS) as measured by ELISA, as described in Example 4. Human IgG1 (hIgG1) was used as a control antibody. EC50/IC50 values were calculated by GraphPad Prism.

MaxiSorp 96-well plates (NUNC #449824, www.thermofisher.com) were coated with 2 µg/ml human IL-25 (R&D systems #1258-IL-025/CF) in 1×PBS (50 µl/well). Plates were incubated at 4° C. overnight. Coating solution was removed and plates were washed once with 200 µl/well PBST (1×PBS with 0.05% tween-20). Then 200 µl/well blocking buffer (1×PBS with 0.05% tween-20, 3% BSA) were added and incubated at room temperature for 1 hour. Blocking buffer was removed and plates were washed three times with 200 µl/well PBST (1×PBS with 0.05% tween-20). Anti-IL-25 antibodies (produced in Example 2) were diluted to 10, 3.33, 1.11, 0.37, 0.123, 0.041, 0.0137, 0.0046, 0.0015, 0.00031, 0.000102, 0.000034 µg/ml by 1×PBS and added to plates (50 µl/well). Plates were incubated at room temperature for 2 hours. Antibodies in the wells were removed and plates were washed three times with 200 µl/well PBST (1×PBS with 0.05% tween-20). Goat anti-human IgG (H&L)-HRP secondary antibody (Jackson Immuno Research #109-035-088, www.jacksonimmuno.com) was diluted 1:5000 in 1×PBS and added to each well (50 µl/well). Plates were incubated at room temperature for 1 hour. Secondary antibody was removed and plates were washed seven times with 200 µl/well PBST (1×PBS with 0.05% tween-20) each time. 50 µl/well TMB (eBioscience #85-00-4201-56, www.ebioscience.com) was added and plates were incubated at room temperature for several minutes. Then 50 µl/well 2N $H_2SO_4$ was added to stop the reaction. Optical density was measured at 450 nm in relation to human IL-25 binding. The equilibrium constant, $EC_{50}$ (nM), was shown in FIG. 2. This result indicates that the anti-IL25 antibodies can bind to human IL-25 with high affinity.

Example 5. Anti-IL-25 Antibody Blocks Inflammatory Cytokine Production Stimulated by Human IL-25

The assay is performed as detection of CXCL1/GROalpha production of HT-29 cells (Chinese Academy of Sciences, #TCHu103) after IL-25 protein (R&D systems #1258-IL-025/CF) stimulation with pre-incubation of anti-IL-25 antibodies (produced in Example 2). HT-29 cells express IL-25 receptor on cell surface. The anti-IL-25 antibodies can block the binding of cytokines to IL-25 receptor and inhibit IL-25-stimulated CXCL1 expression. CXCL1 released in the culture supernatant can be detected by ELISA. Measurement for CXCL1 can indicate the inhibition effect of the anti-IL-25 antibodies.

Figure 3:
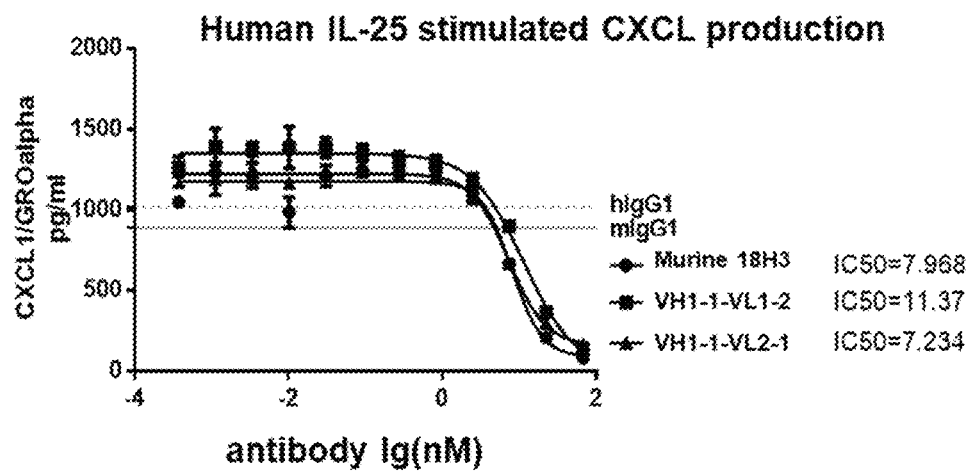
FIG. 3 illustrates the anti-IL-25 antibodies block the inflammatory cytokine CXCL1 production stimulated by human IL-25, as described in Example 5. Human IgG1 (hIgG1) and murine IgG1 (mIgG1) were used as control antibodies. EC50/IC50 values were calculated by GraphPad Prism.
Figure 3:
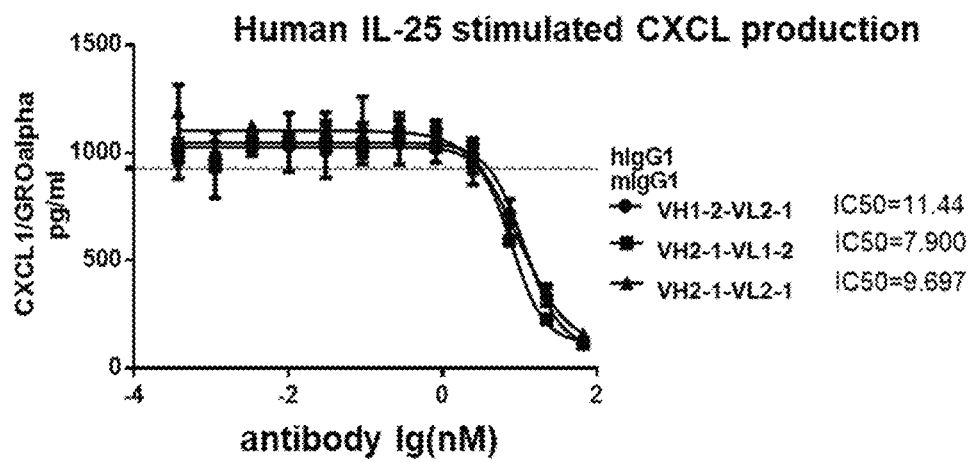

HT29 cells were seeded in 96-well plate with a cell density of $1.0 \times 10^4$ cells/well in 0.2 ml/well McCoy's 5A (Modified) medium with 10% FBS (commercially available from ThermoFisher Scientific), 1% penicillin streptomycin (PS, commercially available from ThermoFisher Scientific). Mixture of anti-IL-25 antibody and hIL-25 was added to the corresponding wells and then the cells were incubated for 48 hours at 37° C. Then the supernatants were harvested for CXCL1 ELISA. CXCL1 measurement was performed by using the kit of Human CXCL1 ELISA Ready-SET-Go (R&D system #DY275). Results were shown in FIG. 3, demonstrating that anti-IL25 antibodies block the stimulated CXCL production induced by the cytokines, thereby inhibiting the development of inflammation.

Example 6. Binding to Human IL-25 and Having No Cross-Reactivity with Other IL-17 Family Members as Measured by ELISA MaxiSorp 96-well plates (NUNC #449824, www.thermofisher.com) were coated with 2 µg/ml human IL-17A (Cell Signaling #89285F, www.cellsignal.com), human IL-17F (Cell Signaling #8906LC, www.cellsignal.com), human IL-17B (Peprotech #200-28, www.peprotech.com), human IL-17C (R&D systems #1234-IL-025/CF, www.rndsystems.com), human IL-17D ((Peprotech #200-27, www.peprotech.com), human IL-17E (R&D systems #1258-IL-025/CF, www.rndsystems.com) in 1×PBS (50 µl/well) respectively. Plates were incubated at 4° C. overnight. Coating solution was removed and plates were washed once with 200 µl/well PBST (1×PBS with 0.05% tween-20). Then 200 µl/well blocking buffer (1×PBS with 0.05% tween-20, 3% BSA) was added and incubated at room temperature for 1 hour. Blocking buffer was removed and plates were washed three times with 200 µl/well PBST (1×PBS with 0.05% tween-20). The anti-IL-25 antibodies (produced in Example 2), were diluted to 10, 3.33, 1.11, 0.37, 0.123, 0.041, 0.0137, 0.0046, 0.0015, 0.00031, 0.000102, 0.000034 µg/ml by 1×PBS and added to the plates (50 µl/well). Plates were incubated at room temperature for 2 hours. Antibodies in the wells were removed and plates were washed three times with 200 µl/well PBST (1×PBS with 0.05% tween-20) each time. Goat anti-human IgG(H&L)-HRP secondary antibody (Jackson Immuno Research #109-035-088, www.jacksonimmuno.com) was diluted 1:5000 in 1×PBS and added to each well (50 µl/well). Plates were incubated at room temperature for 1 hour. Secondary antibody was removed and plates were washed seven times with 200 µl/well PBST (1×PBS with 0.05% tween-20) each time. 50 µl/well TMB (eBioscience #85-00-4201-56, www.ebioscience.com) was added and plates were incubated at room temperature for several minutes. Then 50 µl/well 2N $H_2SO_4$ was added to stop the reaction. Plates were read at 450 nm. Results are showed in Table 2. The anti-IL-25 antibodies have binding ability to IL-25, but do not bind to human IL-17A, 17B, 17C, 17D or 17F, thus having no cross-reactivity with other IL-17 family members.

TABLE 2

Binding ability to IL-17 family members (EC50)

| Anti-IL-17A/F antibody | Binding EC$_{50}$ (nM) | | | | | |
|---|---|---|---|---|---|---|
| | IL-17A | IL-17B | IL-17C | IL-17D | IL-25 | IL-17F |
| VH1-1 – VL2-1 | 0 | 0 | 0 | 0 | 0.15 | 0 |
| VH1-1 – VL1-2 | 0 | 0 | 0 | 0 | 0.25 | 0 |
| VH2-1 – VL2-1 | 0 | 0 | 0 | 0 | 0.187 | 0 |
| VH2-1 – VL1-2 | 0 | 0 | 0 | 0 | 0.196 | 0 |

Example 7. Cross-Reactivity with Mouse and Cynomolgus IL-25 (Binding Assay)

Figure 4:
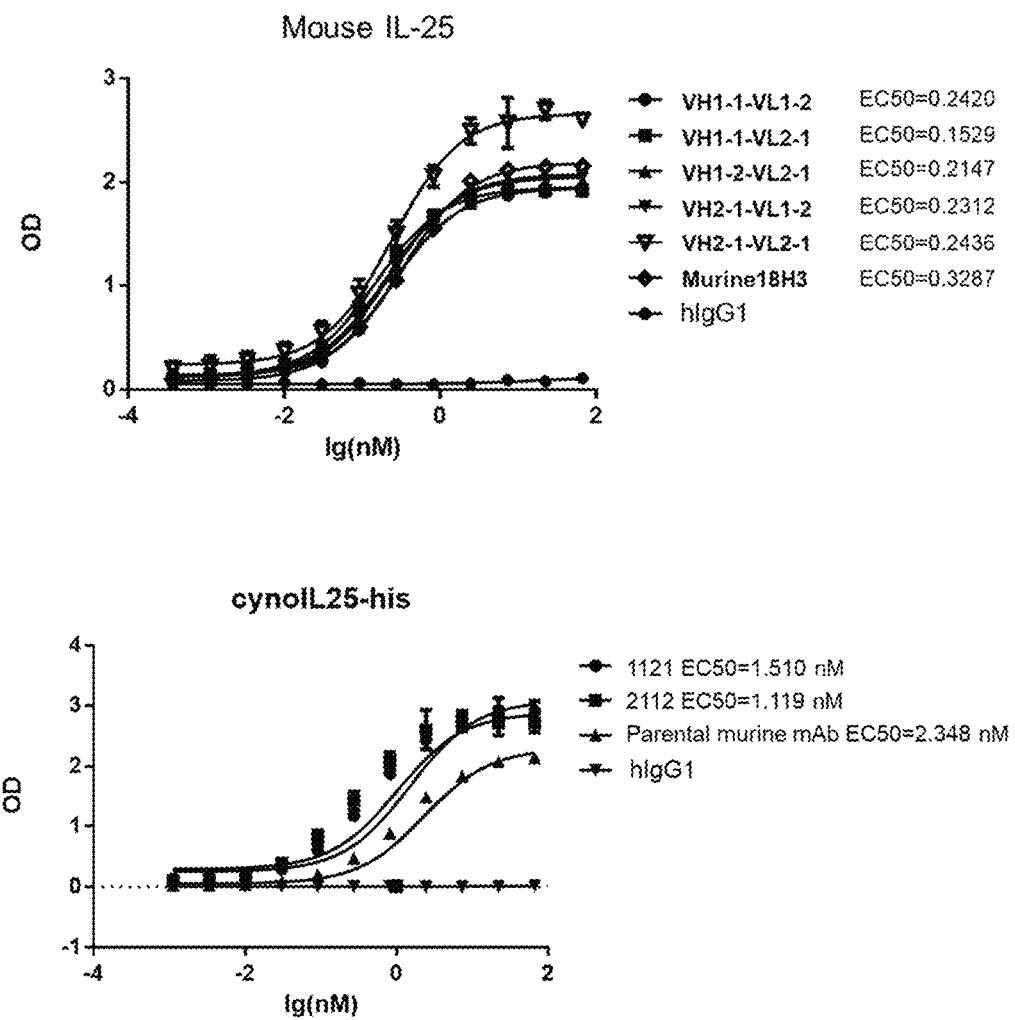
FIG. 4 illustrates the anti-IL-25 antibodies bind to human IL-25 and have no cross-reactivity with other members of IL-17 family, but have cross-reactivity with mouse and cynomolgus IL-25 as measured by ELISA, as described in Examples 6 and 7. The parental murine mAb in the figure is murine 18H3. "1121" in the figure represents the antibody formed by VH1-1 and VL2-1, and "2112" in the figure represents the antibody formed by VH2-1 and VL1-2. Human IgG1 (hIgG1) was used as a control antibody. EC50/IC50 values were calculated by GraphPad Prism.

The binding of anti-IL-25 antibodies to mouse and cynomolgus IL-25 was determined by ELISA. Assay was performed by the same method of Example 6, except that cynomolgus IL-25 (Gene ID: XM_005560861, in-house production according to standard molecular biology method, Carson S, Molecular Biology Techniques, 2012) and mouse IL-25 (Gene ID: AF458060.1, in-house production according to standard molecular biology method, Carson S, Molecular Biology Techniques, 2012) were used to replace human IL-25, respectively. As shown in FIG. 4, the anti-IL25 antibodies have binding ability to both mouse and cynomolgus IL-25, and thus can be used in murine and cynomolgus animal diseases models.

The cross-reactivity to cynomolgus IL-25 indicates that the mouse and cynomolgus monkey are qualified for pharmacokinetics, pharmacodynamics and toxicology studies of the anti-IL-25 antibodies. It is advantageous to develop the anti-IL-25 antibodies as a pharmaceutical composition.

Example 8. In Vivo Animal Studies of the Effect of Anti-IL-25 Antibody

Allergic asthma is characterized by uncontrollable airway hyperresponsiveness (AHR) induced by a variety of provocative stimuli and is associated with type 2 inflammatory infiltrates into the lungs. Type 2 immune responses are characterized by the presence of a CD4+ TH2 cell subset producing cytokines including IgE, IL-4, IL-5, and IL-13. Interleukin (IL)-25 (IL-17E) has been proven to play an important role in the pathogenesis of asthma. Overexpression or exogenous administration of IL-25 reproduces features of asthma pathophysiology in vivo, including epithelial cell hyperplasia, mucus hypersecretion and airway hyperactivity.

Figure 5:
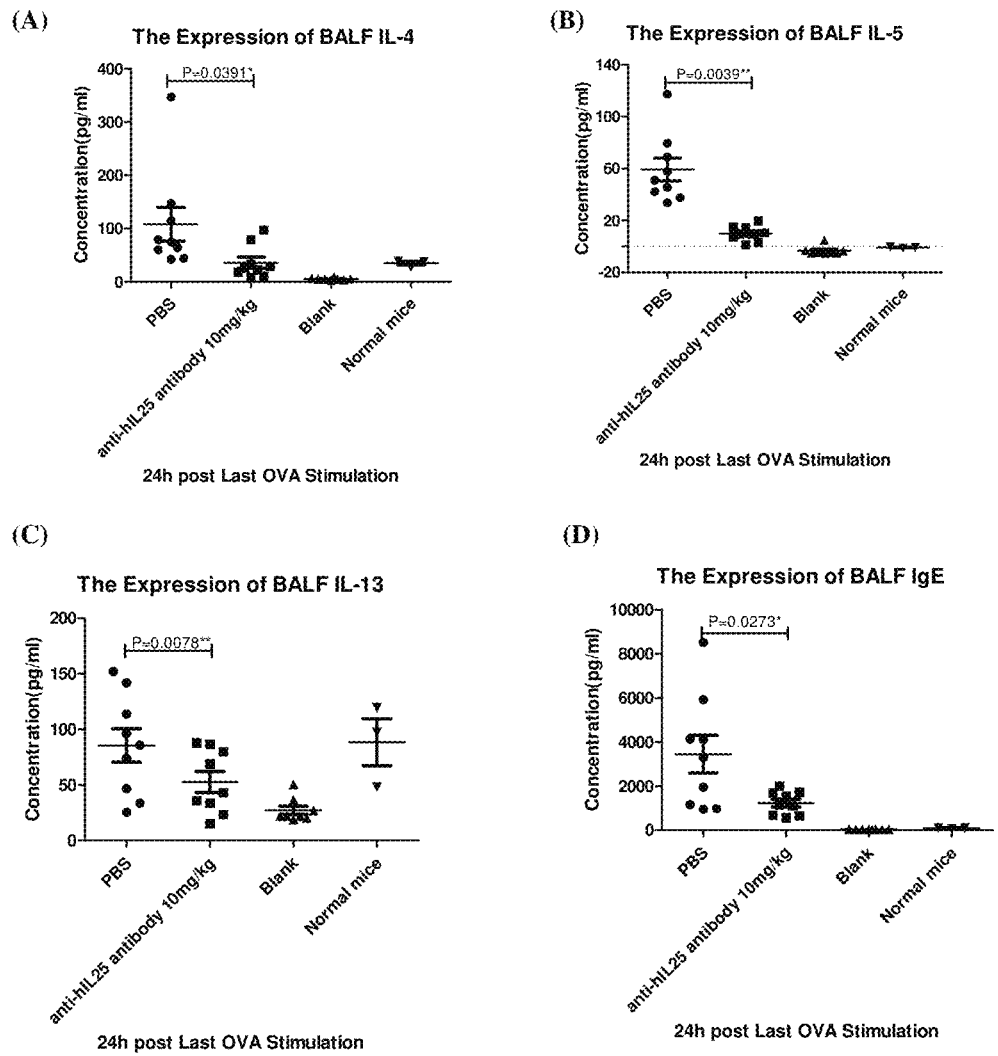
FIG. 5 illustrates in vivo effect of anti-IL-25 antibodies in animal body, as described in Example 8.

The in vivo efficacy of anti-IL-25 antibody (18H3) was studied in the treatment of OVA-induced asthma model in C57BL6J mice (n=5 per group, 8 weeks old, body weight: 18-20 g, commercially available from Beijing Vital River Laboratory Animal Technology Co., Ltd.). On day 1, all mice were subjected to intraperitoneal injection of Chicken Ovalbumin 0.5 mg/ml in alum, 200 µl per mouse (1 mg/ml OVA made in PBS, filter sterilized, mixed with alum 1:1 ratio then vortexed for 1 hr). On day 17, the second IP immunization (same protocol as Day 1) was applied to all mice and the 1st intranasal injection of ovalbumin in PBS, 50 µl (100 µg) OVA was administered to anesthetized mice (2 mg/ml OVA made in PBS, filter sterilized, 50 µl per mice). On day 25, 26, 27, the intranasal injection was repeated daily, and on Day 28, mice were sacrificed <24 hours after the last injection. For PBS and anti-IL25 antibody 18H3 (anti-hIL25 antibody in FIG. 5), the dosing volume was adjusted based on body weight (10 µl/g). The in vivo study design was shown in Table 3. The serum samples were prepared by centrifugation (8000 rpm, 10 min) from blood collected from the mice, and stored at −80° C. until analysis. BALF (bronchoalveolar lavage fluid) collection: Animals were killed with a lethal dose of pentobarbital sodium (150 mg/kg) and the right lungs were ravaged at once with 0.7 cold PBS, and collected about 0.5 ml for BALF. Then, the BALF was centrifuged at 2500 rpm for 5 mins, the supernatant was collected and stored at −80° C. until analysis. The serum and BALF samples were used for cytokine IL-4, IL-5 IL-13 and IgE measurement (the measurement kit for these cytokines were commercial available from eBioscience). As shown in FIG. 5, the anti-IL25 antibody 18H3 inhibited IL-4, IL-13, IL-5 and IgE production in the asthma animal model. The data suggest that anti-IL-25 antibody could be used for the treatment of autoimmune and inflammation disease (i.e. asthma) where these cytokines and/or IgE were elevated.

TABLE 3

| Group | Number of animals | Treatment | Dose (mg/kg) | Dosing Route | Dosing Schedule |
|---|---|---|---|---|---|
| 1 | 9 | PBS | — | s.c. | Q3d × 4 |
| 2 | 10 | anti-hIL25 antibody | 10 | i.v. | Q3d × 4 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An anti-interleukin 25 (IL-25) antibody comprising a heavy chain variable region and a light chain variable region, wherein
the heavy chain variable region comprises a complementary determining region 1 (CDR1) having the amino acid sequence GFSLSTSGMGLG (SEQ ID NO: 1), a CDR2 having the amino acid sequence HIWWDDVKHYKPALKS (SEQ ID NO: 2), and a CDR3 having the amino acid sequence MGQLHYYGYDYAMDY (SEQ ID NO: 3); and
the light chain variable region comprises a CDR1 having the amino acid sequence SASSSVSYMY (SEQ ID NO: 4), a CDR2 having the amino acid sequence RTSNLAS (SEQ ID NO: 5), and a CDR3 having the amino acid sequence QLYHSYPPTWT (SEQ ID NO: 6).

2. The anti-IL-25 antibody according to claim 1, wherein the heavy chain variable region has at least 80%, at least 85%, at least 90%, or at least 95% sequence identity with the amino acid sequence of SEQ ID NO: 12; or the light chain variable region has at least 80%, at least 85%, at least 90%, or at least 95% sequence identity with the amino acid sequence of SEQ ID NO: 13.

3. The anti-IL-25 antibody according to claim 1, wherein the heavy chain variable region comprises the amino acid sequence of SEQ ID NO: 7, SEQ ID NO: 8, SEQ ID NO: 9 or SEQ ID NO: 12; or the light chain variable region comprises the amino acid sequence of SEQ ID NO: 10, SEQ ID NO: 11 or SEQ ID NO: 13.

4. The anti-IL-25 antibody according to claim 3, wherein:
i) the heavy chain variable region comprises the amino acid sequence of SEQ ID NO: 7, and the light chain variable region comprises the amino acid sequence of SEQ ID NO: 10;
ii) the heavy chain variable region comprises the amino acid sequence of SEQ ID NO: 7, and the light chain variable region comprises the amino acid sequence of SEQ ID NO: 11;
iii) the heavy chain variable region comprises the amino acid sequence of SEQ ID NO: 8, and the light chain variable region comprises the amino acid sequence of SEQ ID NO: 10;
iv) the heavy chain variable region comprises the amino acid sequence of SEQ ID NO: 8, and the light chain variable region comprises the amino acid sequence of SEQ ID NO: 11;
v) the heavy chain variable region comprises the amino acid sequence of SEQ ID NO: 9, and the light chain variable region comprises the amino acid sequence of SEQ ID NO: 10;
vi) the heavy chain variable region comprises the amino acid sequence of SEQ ID NO: 9, and the light chain variable region comprises the amino acid sequence of SEQ ID NO: 11; or
vii) the heavy chain variable region comprises the amino acid sequence of SEQ ID NO: 12, and the light chain variable region comprises the amino acid sequence of SEQ ID NO: 13.

5. The anti-IL-25 antibody according to claim 1, which is a monoclonal antibody, a murine antibody, a chimeric antibody, or a humanized antibody.

6. The anti-IL-25 antibody according to claim 1, which is an antibody fragment that binds IL-25, the antibody fragment being selected from the group consisting of Fab, Fab', F (ab') 2, Fv, scFv, Fab-SH, Fab'-SH, Fab-C, Fab'-C, Fab-C-SH, Fab'-C-SH, and diabody.

7. The anti-IL-25 antibody according to claim 1, wherein the antibody is a scFv.

8. The anti-IL-25 antibody according to claim 1, which is of IgG class.

9. The anti-IL-25 antibody according to claim 1, wherein the IL-25 is human IL-25.

10. A pharmaceutical composition comprising the antibody of claim 1 and a pharmaceutically acceptable carrier.

11. An isolated nucleic acid encoding the antibody of claim 1.

12. A host cell comprising the nucleic acid of claim 11.

13. A method of producing the antibody of claim 1 comprising culturing the host cell of claim 12 so that the antibody is produced.

* * * * *

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial sequence
<220> FEATURE:
<223> OTHER INFORMATION: CDR1H amino acid sequence

<400> SEQUENCE: 1

Gly Phe Ser Leu Ser Thr Ser Gly Met Gly Leu Gly
1               5                   10
```

```
<210> SEQ ID NO 2
<211> LENGTH: 16
<212> TYPE: PRT
<213> ORGANISM: Artificial sequence
<220> FEATURE:
<223> OTHER INFORMATION: CDR2H amino acid sequence

<400> SEQUENCE: 2

His Ile Trp Trp Asp Asp Val Lys His Tyr Lys Pro Ala Leu Lys Ser
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: CDR3H amino acid sequence

<400> SEQUENCE: 3

Met Gly Gln Leu His Tyr Tyr Gly Tyr Asp Tyr Ala Met Asp Tyr
1               5                   10                  15

<210> SEQ ID NO 4
<211> LENGTH: 10
<212> TYPE: PRT
<213> ORGANISM: Artificial sequence
<220> FEATURE:
<223> OTHER INFORMATION: CDR1L amino acid sequence

<400> SEQUENCE: 4

Ser Ala Ser Ser Ser Val Ser Tyr Met Tyr
1               5                   10

<210> SEQ ID NO 5
<211> LENGTH: 7
<212> TYPE: PRT
<213> ORGANISM: Artificial sequence
<220> FEATURE:
<223> OTHER INFORMATION: CDR2L amino acid sequence

<400> SEQUENCE: 5

Arg Thr Ser Asn Leu Ala Ser
1               5

<210> SEQ ID NO 6
<211> LENGTH: 11
<212> TYPE: PRT
<213> ORGANISM: Artificial sequence
<220> FEATURE:
<223> OTHER INFORMATION: CDR3L amino acid sequence

<400> SEQUENCE: 6

Gln Leu Tyr His Ser Tyr Pro Pro Thr Trp Thr
1               5                   10

<210> SEQ ID NO 7
<211> LENGTH: 125
<212> TYPE: PRT
<213> ORGANISM: Artificial sequence
<220> FEATURE:
<223> OTHER INFORMATION: Variable heavy chain domain (VH1-1) amino acid
      sequence

<400> SEQUENCE: 7

Gln Val Thr Leu Lys Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Thr Ser
            20                  25                  30

Gly Met Gly Leu Gly Trp Ile Arg Gln Pro Pro Gly Lys Ala Leu Glu
        35                  40                  45

Trp Leu Ala His Ile Trp Trp Asp Asp Val Lys His Tyr Lys Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Val Asp Pro Val Asp Thr Ala Thr Tyr Tyr
                85                  90                  95

Cys Ala Arg Met Gly Gln Leu His Tyr Tyr Gly Tyr Asp Tyr Ala Met
                100                 105                 110

Asp Tyr Trp Gly Gln Gly Thr Leu Val Thr Val Ser Ser
        115                 120                 125

<210> SEQ ID NO 8
<211> LENGTH: 125
<212> TYPE: PRT
<213> ORGANISM: Artificial sequence
<220> FEATURE:
<223> OTHER INFORMATION: Variable heavy chain domain (VH2-1) amino acid
      sequence

<400> SEQUENCE: 8

Gln Val Thr Leu Arg Glu Ser Gly Pro Ala Leu Leu Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Leu Gly Trp Ile Arg Gln Pro Pro Gly Lys Ala Leu Glu
        35                  40                  45

Trp Leu Ala His Ile Trp Trp Asp Asp Val Lys His Tyr Lys Pro Ala
50                  55                  60

Leu Lys Ser Arg Leu Thr Ile Ser Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Met Gly Gln Leu His Tyr Tyr Gly Tyr Asp Tyr Ala Met
                100                 105                 110

Asp Tyr Trp Gly Gln Gly Thr Leu Val Thr Val Ser Ser
        115                 120                 125

<210> SEQ ID NO 9
<211> LENGTH: 144
<212> TYPE: PRT
<213> ORGANISM: Artificial sequence
<220> FEATURE:
<223> OTHER INFORMATION: Variable heavy chain domain (VH1-2) amino acid
      sequence

<400> SEQUENCE: 9

Met Gly Trp Ser Trp Ile Leu Leu Phe Leu Leu Ser Val Thr Ala Gly
1               5                   10                  15

Val His Ser Gln Val Thr Leu Lys Glu Ser Gly Pro Thr Leu Leu Lys
            20                  25                  30

Pro Thr Gln Thr Leu Thr Leu Thr Cys Thr Phe Ser Gly Phe Ser Leu
        35                  40                  45

Ser Thr Ser Gly Met Gly Leu Gly Trp Ile Arg Gln Pro Pro Gly Lys
50                  55                  60
```

```
Ala Leu Glu Trp Leu Ala His Ile Trp Trp Asp Val Lys His Tyr
 65                  70                  75                  80

Lys Pro Ala Leu Lys Ser Arg Leu Thr Ile Thr Lys Asp Thr Ser Lys
                 85                  90                  95

Asn Gln Val Val Leu Thr Ile Thr Asn Val Asp Pro Val Asp Thr Ala
            100                 105                 110

Thr Tyr Tyr Cys Ala Arg Met Gly Gln Leu His Tyr Tyr Gly Tyr Asp
        115                 120                 125

Tyr Ala Met Asp Tyr Trp Gly Gln Gly Thr Leu Val Thr Val Ser Ser
    130                 135                 140
```

```
<210> SEQ ID NO 10
<211> LENGTH: 108
<212> TYPE: PRT
<213> ORGANISM: Artificial sequence
<220> FEATURE:
<223> OTHER INFORMATION: Variable light chain domain (VL2-1) amino acid
      sequence

<400> SEQUENCE: 10

Asp Ile Gln Leu Thr Gln Ser Pro Ser Phe Leu Ser Ala Ser Val Gly
 1               5                  10                  15

Asp Arg Val Thr Ile Thr Cys Ser Ala Ser Ser Val Ser Tyr Met
                 20                  25                  30

Tyr Trp Tyr Gln Gln Lys Pro Gly Lys Ala Pro Lys Pro Leu Ile Tyr
             35                  40                  45

Arg Thr Ser Asn Leu Ala Ser Gly Val Pro Ser Arg Phe Ser Gly Ser
 50                  55                  60

Gly Ser Gly Thr Glu Tyr Thr Leu Thr Ile Ser Ser Met Gln Pro Glu
 65                  70                  75                  80

Asp Phe Ala Thr Tyr Tyr Cys Gln Leu Tyr His Ser Tyr Pro Pro Thr
                 85                  90                  95

Trp Thr Phe Gly Gln Gly Thr Lys Leu Glu Ile Lys
             100                 105
```

```
<210> SEQ ID NO 11
<211> LENGTH: 108
<212> TYPE: PRT
<213> ORGANISM: Artificial sequence
<220> FEATURE:
<223> OTHER INFORMATION: Variable light chain domain (VL1-2) amino acid
      sequence

<400> SEQUENCE: 11

Glu Ile Val Leu Thr Gln Ser Pro Ala Thr Leu Ser Ala Ser Pro Gly
 1               5                  10                  15

Glu Arg Val Thr Ile Ser Cys Ser Ala Ser Ser Val Ser Tyr Met
                 20                  25                  30

Tyr Trp Tyr Gln Gln Lys Pro Gly Gln Ala Pro Arg Pro Leu Ile Tyr
             35                  40                  45

Arg Thr Ser Asn Leu Ala Ser Gly Val Pro Ala Arg Phe Ser Gly Ser
 50                  55                  60

Gly Ser Gly Thr Asp Tyr Thr Leu Thr Ile Ser Ser Met Glu Pro Glu
 65                  70                  75                  80

Asp Phe Ala Thr Tyr Tyr Cys Gln Leu Tyr His Ser Tyr Pro Pro Thr
                 85                  90                  95

Trp Thr Phe Gly Gln Gly Thr Lys Leu Glu Ile Lys
             100                 105
```

```
<210> SEQ ID NO 12
<211> LENGTH: 125
<212> TYPE: PRT
<213> ORGANISM: Artificial sequence
<220> FEATURE:
<223> OTHER INFORMATION: Amino acid sequence of variable heavy chain of
      18H3

<400> SEQUENCE: 12

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Gly Trp Ile Arg Gln Pro Ser Gly Lys Gly Leu Glu
        35                  40                  45

Trp Leu Ala His Ile Trp Trp Asp Asp Val Lys His Tyr Lys Pro Ala
    50                  55                  60

Leu Lys Ser Arg Leu Thr Ile Ser Lys Asp Ile Ser Ser Ser Gln Val
65                  70                  75                  80

Phe Leu Thr Ile Ala Ser Val Asp Thr Ala Asp Thr Ala Thr Tyr Tyr
                85                  90                  95

Cys Ala Arg Met Gly Gln Leu His Tyr Tyr Gly Tyr Asp Tyr Ala Met
            100                 105                 110

Asp Tyr Trp Gly Gln Gly Thr Ser Val Thr Val Ser Ser
            115                 120                 125

<210> SEQ ID NO 13
<211> LENGTH: 108
<212> TYPE: PRT
<213> ORGANISM: Artificial sequence
<220> FEATURE:
<223> OTHER INFORMATION: Amino acid sequence of variable light chain of
      18H3

<400> SEQUENCE: 13

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Leu Tyr His Ser Tyr Pro Pro Thr
                85                  90                  95

Trp Thr Phe Gly Gly Gly Thr Lys Leu Glu Ile Lys
            100                 105
```